US006269703B1

(12) United States Patent
Bowers

(10) Patent No.: US 6,269,703 B1
(45) Date of Patent: *Aug. 7, 2001

(54) PULSED AIR SAMPLER

(75) Inventor: William D. Bowers, Newport Beach, CA (US)

(73) Assignee: Femtometrics, Inc., Irvine, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/151,743

(22) Filed: Sep. 11, 1998

(51) Int. Cl.[7] .................................................. G01N 25/18
(52) U.S. Cl. .......................................................... 73/863.12
(58) Field of Search ........................... 73/863.11, 863.12, 73/863.33, 864, 864.33, 864.34, 864.71, 863.21–863.24, 864.81–864.85

(56) References Cited

U.S. PATENT DOCUMENTS

| 3,362,141 | | 1/1968 | Royster, Jr. et al. . | |
|---|---|---|---|---|
| 4,896,547 | * | 1/1990 | Arney et al. . | |
| 4,909,089 | * | 3/1990 | Archter et al. ..................... | 73/863.11 |
| 4,909,090 | * | 3/1990 | McGown et al. .................. | 74/864.33 |
| 5,092,157 | * | 3/1992 | Achter et al. ...................... | 73/863.12 |
| 5,162,652 | | 11/1992 | Cohen et al. . | |
| 5,253,538 | | 10/1993 | Swick et al. . | |
| 5,476,002 | | 12/1995 | Bowers et al. . | |
| 5,551,278 | | 9/1996 | Rounbehler et al. . | |
| 5,741,984 | * | 4/1998 | Danylewych-May et al. ... | 73/864.71 |
| 5,753,832 | * | 5/1998 | Bromberg et al. ................ | 73/864.81 |
| 5,970,803 | * | 10/1999 | Staples et al. ..................... | 73/863.12 |

FOREIGN PATENT DOCUMENTS

| 0 896 213 A2 | 2/1999 | (EP) . |
|---|---|---|
| WO 97/35174 | 9/1997 | (WO) . |

OTHER PUBLICATIONS

AEC–NASA TECH BRIEF, Brief 68–10231.*
The How and Why of Electronic Noses, IEEE Spectrum, Sep. 1998.

* cited by examiner

Primary Examiner—Robert Raevis
(74) Attorney, Agent, or Firm—Knobbe, Martens, Olson & Bear, LLP

(57) ABSTRACT

A device samples chemicals adsorbed to a surface by applying a pulse of fluid to desorb the particles adhered to the surface. After the pulse of fluid, the region above the surface is enriched with particles dislodged from the surface. Suction is applied in the region above the surface to collect these dislodged particles, which are then transferred to a chemical detector for detection, identification, and quantification.

A pulsed air sampler collects particles adhered to a surface and delivers the particles to a chemical sensor. An outlet ejects a fluid, preferably gas, pulse to dislodge particles from the surface and thereby enrich the density of particles above the surface. An inlet collects the dislodged particles for delivery to the chemical sensor.

38 Claims, 4 Drawing Sheets

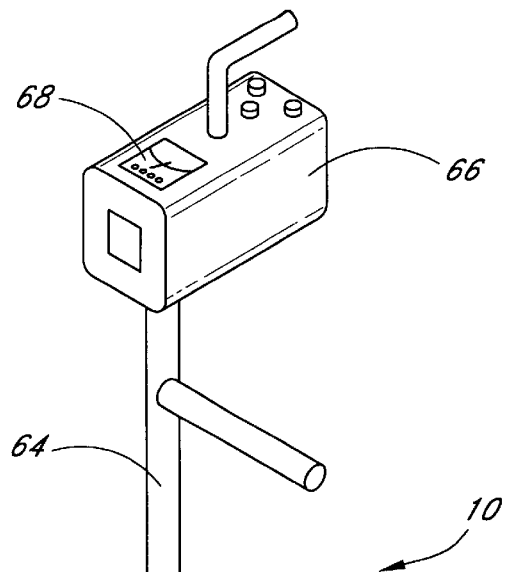
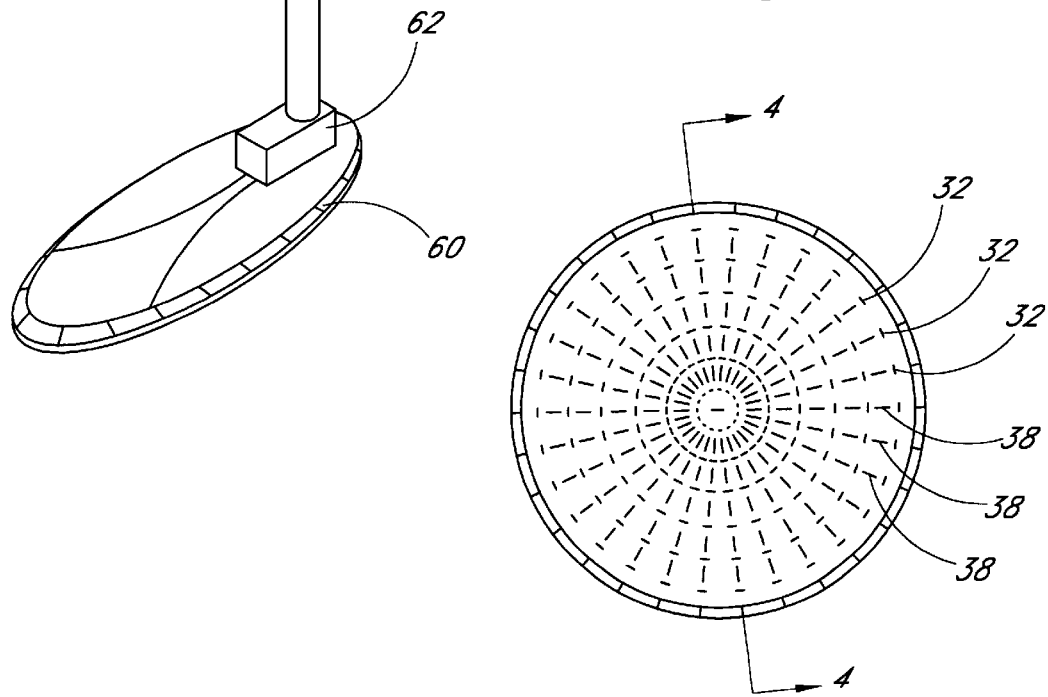

PULSED AIR SAMPLER

BACKGROUND OF THE INVENTION

The present invention relates to an apparatus for collecting chemical samples, and more specifically, to an apparatus that is capable of collecting particles or molecules adhered to a surface.

Many situations arise requiring the capability to detect the presence or absence of a chemical on a surface. One important example is the detection of toxic and hazardous substances in the environment, such as explosives and chemical agents. Searching for toxic or hazardous substances involves monitoring a variety of different surfaces and checking for the presence of particular chemicals.

In general, the process of detecting a chemical comprises three main steps: acquiring the sample, conditioning the sample, and employing a chemical detector to detect, identify and quantify the specific chemical of interest, herein referred to as the target analyte or target. Sample acquisition comprises the removal of the target analyte from a surface or host matrix to which it may be attached. Sample conditioning comprises the preparation, conditioning, or processing of the sample prior to its introduction to a chemical detector. Detecting the target analyte with the chemical detector involves determining the presence or absence of the target chemical on or in the chemical detector.

Although chemical detection is conventionally viewed as being defined by the lower limit of the detection ability of the chemical detector, the performance of the chemical detector alone does not accurately characterize the ability of the entire system to detect the presence of a specific chemical. In many cases, performance is significantly affected by sample acquisition and conditioning.

Often, it is difficult to acquire a chemical sample when the chemical is adhered to a surface, particularly if the vapor pressure of the chemical is low, or if the temperature is low. Under these circumstances, only a small amount of molecules may be in the gas phase and available for collection. Additionally, the surface of the chemical may become crusted-over with time, which further reduces the quantity of vapors in the gas phase available for detection.

Accordingly, a need exists for an improved system for collecting chemical samples, particularly when the chemical is adhered to a surface.

SUMMARY OF THE INVENTION

The present invention comprises an apparatus for collecting particles, such as molecules, that are adhered to a surface. The apparatus comprises an outlet that ejects fluid for dislodging the particles from the surface and an inlet for collecting the particles once dislodged. The particles may, for example, be in the form of an aerosol or vapor.

In the preferred embodiment, the fluid is warm air and a plurality of outlets are employed to eject pulses of the warm air. A blower draws air from the atmosphere and supplies that air to the outlets to dislodge or desorb the particles while a pump provides suction to draw the particles into a plurality of inlets. Intermittent flow of air through the outlets may be achieved by means of a valve, or alternatively, by blower control electronics that switch the blower on and off. Intermittent suction at the inlets may be provided by activating the pump intermittently or, alternatively, by using a valve.

According to another aspect of the invention, a method for collecting particles, such as molecules, that are adhered to a surface comprises ejecting fluid onto the surface to desorb the particles from the surface and drawing the desorbed particles into an inlet. The particles can then be detected using a chemical detector. In the preferred embodiment, the ejected fluid comprises pulses of air which are diverted against the surface and the drawing is accomplished using intermittent suction. Such ejection may be alternated with the drawing. In another embodiment, continuous suction is provided throughout a plurality of blowing periods. In the preferred embodiment, the fluid as well as the desorbed particles are heated. For example, the desorbed particles may be heated by heating the inlet. Preferably, the fluid directs the desorbed particles toward the inlet.

BRIEF DESCRIPTION OF THE DRAWINGS

FIG. 1. is a perspective view of a preferred embodiment of the present invention.

FIG. 2 is a plan view of the bottom of the embodiment of FIG. 1 showing the plurality of inlet and outlet orifices arranged in concentric arrays.

DETAILED DESCRIPTION OF THE PREFERRED EMOBIDMENT

Figure 3:
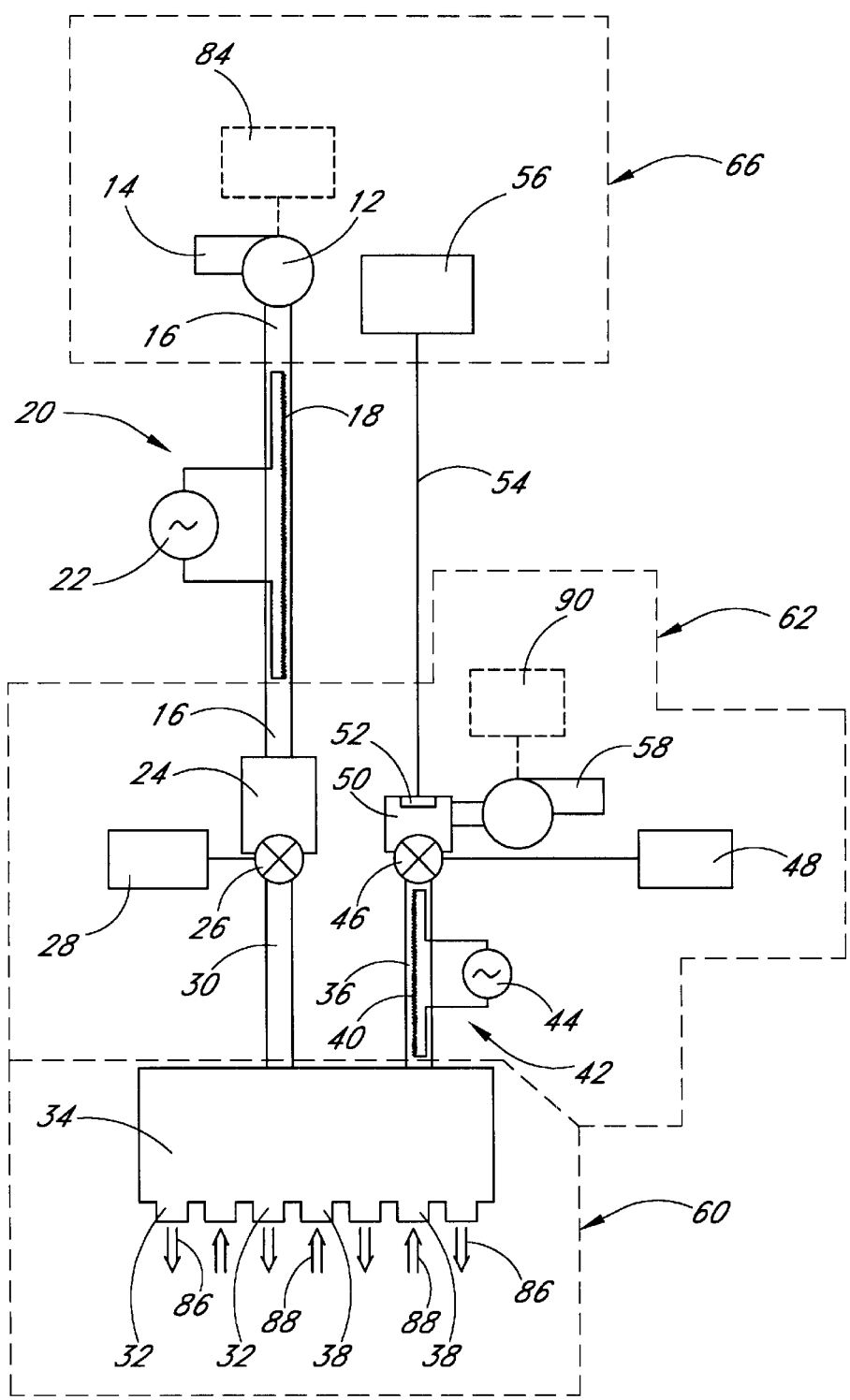
FIG. 3 is a schematic drawing of the embodiment of FIGS. 1 and 2.

As illustrated in FIG. 1, a pulsed air sampler 10 comprises a display assembly 66 having a display and/or alarm 68. The display assembly 66 is mounted on one end of a shaft 64 and contains a master CPU. The other end of the shaft 64 is connected to an interface assembly 62. A collector assembly 60 is attached to the interface assembly 62. The pulsed air sampler 10 is powered entirely by batteries located in the display assembly, and thus is completely portable.

As shown in FIG. 2, the collector assembly 60 includes an array of inlet orifices or inlets 38 and an array of outlet orifices or outlets 32. The inlets 38 are interspersed with the outlets 32 to form a pattern in which each inlet 38 is located between an adjacent pair of outlets 32, such that the outlets and inlets are in concentric arrays.

As shown in FIG. 3, the display assembly 66 comprises an air blower 12 with an air intake or inlet 14 and an air outlet attached to a pneumatic conduit 16 that extends through the shaft 64. An outlet heater 20 has a heating element 18 in thermal contact with the conduit 16. The heater 20 includes a heater power supply 22. The pneumatic line 16 conducts air from the inlet 14 to a chamber 24 in the interface assembly 62. The chamber 24 has an outlet valve 26 electrically connected to electronics 28 to control air flow to an outlet line 30. The outlet line 30 conducts air from the valve 26 to an air flow distribution network 34 in the collector assembly 60.

The air travels through a manifold (FIG. 4) in the network 34 and is output from the plurality of outlets 32.

The air distribution network 34 additionally comprises a second manifold (FIG. 4) that conducts air from the plurality of inlets 38 to an inlet line 36. An inlet heater 42 comprises a heater power supply 44 and a heater element 40 that is in thermal contact with the inlet line 36. The inlet line 36 is attached to an inlet valve 46 within the interface assembly 62. The valve 46 is electrically connected to valve control electronics 48 to control flow from the inlet line 36 to a detector housing 50 in the interface 62. The detector housing 50 contains a chemical detector, such as a sensor 52. Electrical cable 54 connects the chemical sensor 52 to detection electronics 56. A sample acquisition pump 58, attached to the detector housing 50 containing the chemical sensor 52, is provided to draw air from the inlets 38 to the sensor 52. Electrical cable 54 connects the chemical sensor 52 to detection electronics 56 in the display assembly 66.

Figure 4:
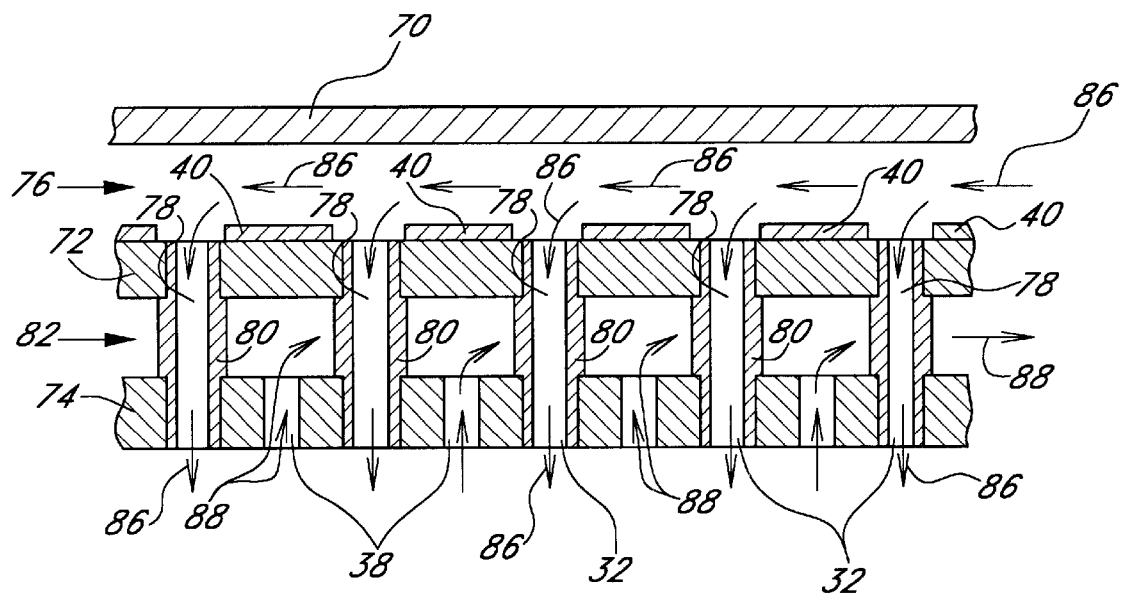
FIG. 4 is a fragmented cross-sectional view taken along the lines 4—4 of FIG. 3 showing the air flow distribution network.

As shown in FIG. 4, the air flow distribution network 34 is comprised of three plates, an upper plate 70, a middle plate 72, and a lower plate 74. The upper plate 70 is spaced from the middle plate 72 to form a passageway or plenum 76 therebetween. This outlet line 30 is connected to the plenum 76 and is in fluid communication therewith. The inlet heater element 40 extends from the conduit 36 into the passageway 76 between the upper plate 70 and the middle plate 72. This heater element 40 is disposed in thermal contact with the middle plate 72. Preferably, the middle plate 72 is formed of a thermally conducting material, such as aluminum, so that application of heat by the heater element causes both the top and bottom surfaces of the middle plate to be warmed. Tubular members or inserts 80 extend from the middle plate 72 to the lower plate 74. The ends of each tubular member 80 have reduced diameter portions which are press fit or glued into openings in the middle plate 72 and lower plate 74, respectively. The bores of the members 80 form respective linear passageways 78 that extend from the plenum 76 to the outlet orifices 32. The tubular members 80 also function as spacers to mount the lower plate 74 in spaced relationship to the middle plate 72. The spacing between the middle plate 72 and the lower plate 74 creates a passageway or plenum 82 between the middle plate 72 and the lower plate 74. This plenum 82 is connected to the inlet line 36, and is in fluid communication therewith. The inlet openings 38 in the lower plate 74 are in fluid communication with the interior of the plenum 82. Thus, the three plates 70, 72, 74 provide two intertwined manifolds, each having a sealed air flow path, one of which extends from the inlets 38 through the plenum 82 to the inlet line 36, and the other of which extends from the outlet line 30, through the plenum 76, through the tubes 80 and to the outlets 32. Air flow from the inlets 38 is illustrated by arrows 88 while air flow to the outlets is illustrated by arrows 86.

In operation, the pulsed air sampler 10 collects particles such as molecules that are adhered to a surface by employing a timed sequence of short air pulses to disturb the layer of molecules at the interface between the surface and the surrounding region of air. The pulses of air have sufficient velocity to both disturb the molecules and to move them away from the surface. In order to facilitate the desorption of the molecules adsorbed to the surface, warm air is used to warm the molecules, and thereby increase their thermal activation energy and enhance the likelihood that they will be desorbed from the surface. After application of an air pulse, the vapor above the surface will be enriched by the desorbed molecules, and the enriched vapor is drawn into the inlets 38 by suction. The enriched vapor may contain aerosols which are comprised of high concentrations of the target molecule.

Air blower 12 generates the air required to dislodge the adsorbed molecules from the surface. The air blower 12 draws ambient air from the air intake 14 and forces the air into the pneumatic line 16 to the accumulation chamber 24. Preferably, the air blower 12 is capable of pressurizing the chamber 24 to a pressure in range of about 0.5 to 5 pounds per square inch (psi) above atmospheric pressure, and provides a flow rate from about 10 to 2000 cubic centimeters of air per minute. The air blower 12 forces air under pressure through the pneumatic line 16 in the shaft 64. The heating element 18 heats the conduit 16 so that the air is heated as it travels down the shaft. The shaft 64 may be surrounded with thermal insulating material to minimize heat loss and conserve power. Preferably, the outlet heating element 18 extends substantially the entire length of the pneumatic line 16 and the shaft 64 (about 3–4 feet in the preferred embodiment).

The pressure within the chamber 24 is released by opening the outlet valve 26. The outlet valve 26 is a spring-loaded gate valve that is controlled by the flow control electronics 28. Alternatively, the blower 12 itself can be switched on and off with a blower controller 84, instead of employing the outlet valve 26.) Once the outlet valve 26 is opened, a pulse of warm air will rush through the outlet line 30 and into the flow distribution network 34 shown in FIG. 4. Specifically, the jets of air flow through the outlet line 30 and into the passageway 76 between the upper plate 70 and the middle plate 72, in the direction of the arrows 86. The air proceeds down the tubular members 80 and through the outlet orifices 32 to dislodge the molecules from the surface being monitored.

The warm air exits the outlets 32 at a sufficient velocity and temperature and in sufficient volume to dislodge the molecules from the surface. The temperature of the air effected from the outlets, for example, may be between about 25° C. and 60° C.

To collect the sample, the pump 58 is activated to provide suction at the inlets 38 dislodged molecules into the inlet line 36 and the detector housing 50. The pump 58 may, for example, draw from 50 to 1000 cubic centimeters of air per minute. Providing suction on the inlet line 36 will cause air to be drawn from the passageway 82 between the middle plate 72 and the lower plate 74. Consequently, air is drawn through the inlet orifices 38 formed in the lower plate 74. Arrows 88 indicate the flow of the air into the inlet orifices 38, through the passageway 82 between the middle plate 72 and the lower plate 74, and into the inlet line 36. The incoming air, enriched with dislodged molecules, travels through the inlet line 36 and into the sensor housing 50.

In some cases, the target molecules may tend to adsorb onto the inlet line 36 or onto the middle 72 and lower plates 74 in the passageway 82 or onto the inlet orifices 38 as the sample is drawn towards the sensor. Such adsorbed molecules will not be detected by the chemical sensor 52 and, thus will result in an inaccurate measurement of the sample concentration. Conversely, random desorption of molecules previously adsorbed on the inlet line 36 or on the middle 72 or lower plates 74 will be detected by the chemical sensor 52 and will also create inaccurate measurements of the sample concentration. Such adsorption and/or desorption can cause measurement errors, particularly when the concentration of molecules is low.

To minimize the adsorption of the molecules onto the surfaces of the inlet orifices 38, the air flow distribution network 34, and the inlet line 36, the incoming air may be heated using the heating element 40 to heat the inlet line 36 and the middle plate 72 (FIG. 4). The inlet heater 42 applies thermal energy to the middle plate 72, which warms the incoming air to a temperature, for example, between about 25° C. and 60° C.

To further minimize adsorption of the dislodged molecules, the inlet line 36, the inlet orifices 38, as well as the sides of the middle 72 and lower 74 plates that form the plenum 82 can be chemically deactivated by applying a coating, such as polytetrafluoroethylene (e.g., Teflon®), which does not provide a reactive surface on which the molecules can adsorb.

In the preferred embodiment, the suction provided to draw the molecules into the inlets 38 is intermittent. The valve 46 situated between the air pump 58 and the inlets 38 is opened and closed to switch the suction on and off. Valve control electronics 48 are employed to open and close the valve 46 in an intermittent fashion. Alternatively, the pump 58 itself can be switched on and off with a pump controller 90.

The suction provided by the pump 58 ultimately transports the dislodged target molecules from the surface being monitored to the sensor housing 50. Once in the sensor housing 50, the molecules can be detected by the chemical sensor 52. It will be appreciated that the chemical sensor 52 may comprise any sensor capable of detecting the presence of the specific molecules or other particles sought to be detected. Well known examples of such chemical sensors 52 include surface acoustic wave, chemi-resistors, and solid-state sensors. A chemical sensor employing an array of SAW devices is disclosed in the co-pending application of William D. Bowers, et al. entitled "Chemical Sensor Array", Ser. No. 09/151,747 filed on the same date as the present application which is hereby incorporated herein by reference.

Preferably, the chemical sensor 52 is capable of identifying as well as detecting the presence of the target molecules or particles. In either case, the chemical sensor 52 outputs an electrical signal that indicates that target molecules have been detected. This electrical signal is carried by electrical cable 54 to the sensor electronics 56 and ultimately to a display 68 in the display assembly 66 shown in FIG. 1.

Although the preferred pulsed air sampler 10 employs air to dislodge molecules adhered to a surface, other fluids, gaseous and liquid, may be employed in separate embodiments of the invention. Additionally, the apparatus of the present invention may be used to detect the presence of particles other than molecules, such as sub micron, neutrally charged particles. These particles may be adhered to either a liquid or solid surface.

Figure 5:
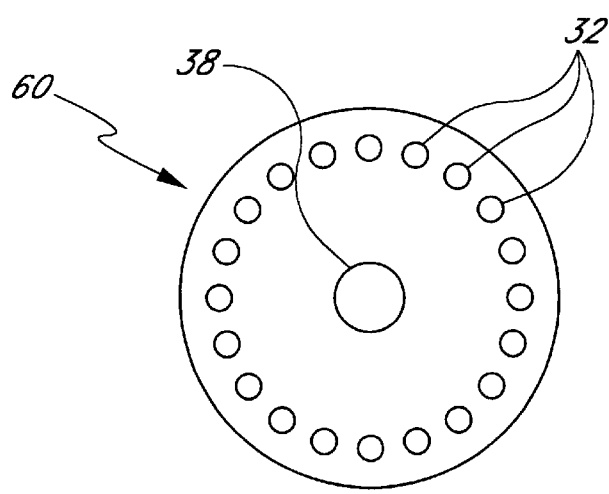
FIG. 5 is a plan view of the bottom of another embodiment of the present invention wherein a plurality of outlet orifices surrounds a single inlet orifice.

As discussed above, in the embodiment shown in FIG. 2, the plurality of inlets 38 as well as the plurality of outlets 32 are arranged in concentric arrays as shown in FIG. 2. The arrays are alternated, each inlet 38 or array of inlets being surrounded by an array of outlets 32. Also, each outlet array, except for the outermost, is surrounded by an array of inlets 38. An alternative configuration is depicted in FIG. 5. In this configuration, a single inlet 38 is surrounded by a single concentric array of outlets 32. FIG. 5 also shows the inlet 38 and outlet 32 orifices as circular openings. In yet another configuration (not shown), a single common inlet/outlet orifice is used in place of separate outlets and inlets. This configuration can be implemented by connecting both the outlet line 30 and the inlet line 36 to a single line terminated by an inlet/outlet orifice. Employing the same hole as both the outlet for ejecting fluid and the inlet for collecting the dislodged particles can minimize false positive readings caused by the desorption of particles stuck to the surface of the orifice or the inlet line 36. Warm fluid exiting from outlet line 30 could remove particles adsorbed onto the walls of the inlet/outlet orifice and carry them away from the chemical sensor 52. Thus, this embodiment may prevent the random desorption of particles adhered to the inlet and detected by the chemical sensor 52, and thereby improve the accuracy of estimates of the concentration of particles on the surface being monitored. As described above, the suction provided to draw the particles into the inlets is preferably intermittent, and the drawing of the particles into the inlets is preferably alternated with the step of blowing air through the outlets.

To test a surface for the presence of the target particle, such as a molecule, the operator moves the pulsed air sampler 10 towards the surface to be monitored. In order to avoid contamination, the bottom of the collector assembly 60 (FIG. 1) should preferably be at least 10–15 mm from the surface to be sensed, so that the molecules do not adhere to it. As described above, a pulse of warm air is emitted from the plurality of outlet orifices 32 thereby dislodging or desorbing the particles on the surface to be sampled. The use of short intermittent output pulses of warm air is preferred, since a continuous flow of warm air onto the surface tends to dilute the sample. By way of example, the pulse duration may be from about a few milliseconds to about one second. The warm air pulse can be controlled either automatically or by the user. The multiple jets of air emerging from the plurality of outlets 32 disturb the molecules residing within the surface/air boundary, causing the molecules to be desorbed from the surface being monitored. The jets are turned off as the target molecules become airborne. These airborne molecules may take the form of chemical vapor or aerosols containing the target molecule. Suction is subsequently provided to draw the air located below the pulsed air sampler 10 into the inlets 38 and to the chemical sensor 52.

Figure 6A:
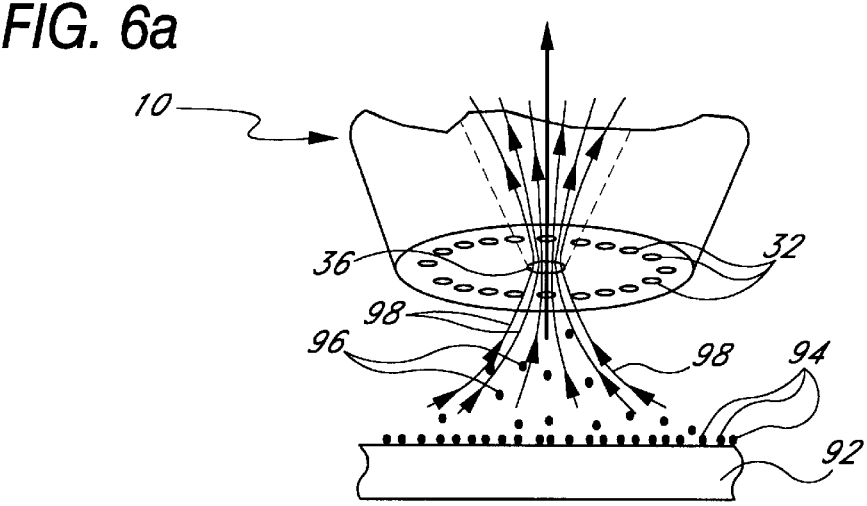
FIG. 6a is an elevational view of the embodiment of FIG. 5 that depicts the application of suction to draw particles into the inlet.
Figure 6B:
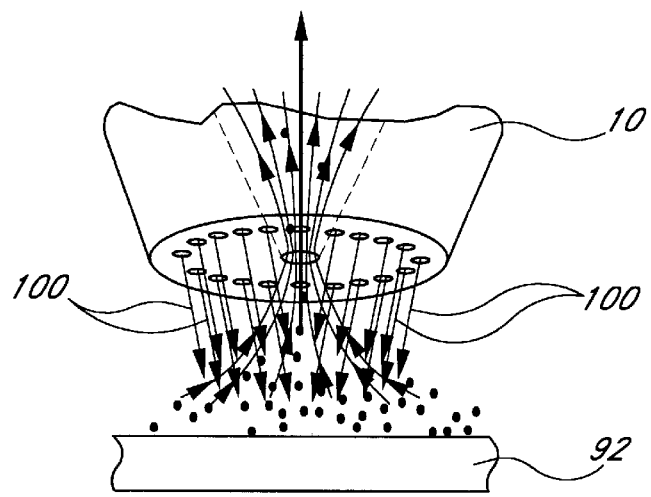
FIG. 6b is an elevation view of the embodiment of FIG. 5 showing fluid exiting the plurality of outlets to dislodge particles adhered to a surface, and showing suction being simultaneously applied to draw the desorbed particles into the inlet.
Figure 6C:
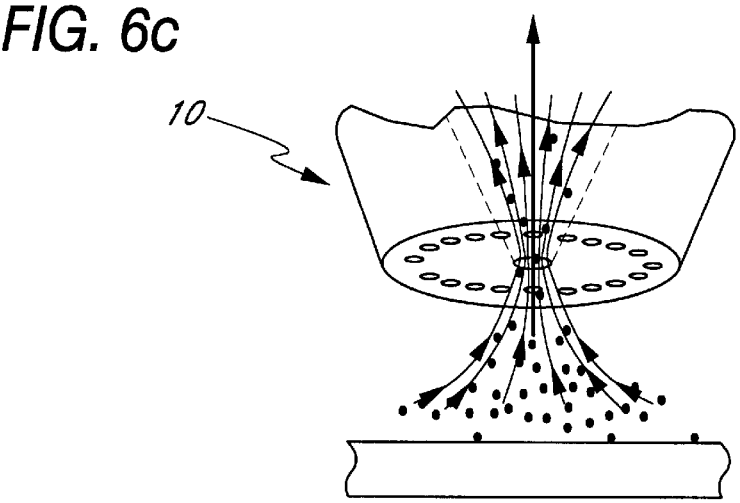
FIG. 6c is an elevation view of the embodiment of FIG. 5 that illustrates the continued application of suction to draw the desorbed particles into the inlet after the fluid ejection shown in FIG. 6b has ceased.

In an alternative preferred embodiment, suction can continuously be applied while fluid, such as warm air, is periodically ejected from the outlets 32. FIG. 6a to 6c show an embodiment of the sampler 10 having a single inlet 38 and a concentric array of outlets 32 situated over a contaminated surface 92. In FIG. 6a, suction has been applied, but fluid has not yet been ejected from the outlets 32. Particles 94 are shown on the contaminated surface 92. A portion 96 of the particles 94 are airborne and are being drawn into the inlet 38 by suction. Lines 98 indicate the flow of the particles 94 toward the inlet 38 as a result of this suction.

In FIG. 6b, suction is being applied while fluid is simultaneously being ejected from the array of outlets 32. Arrows 100 indicate the flow of fluid ejected from the outlets 32. FIG. 6b depicts the situation where the pulse of fluid dislodges or desorbs the particles 94 and yet does not dilute the sample. In particular, the particles 94 that are shown in FIG. 6a on the surface 92 are portrayed as airborne in FIG. 6b as a result of the pulse of fluid emanating from the plurality of outlets 32. FIG. 6b additionally shows suction being applied and the particles 94 that are dislodged or desorbed from the surface 92 being drawn into the inlet 38. As discussed above, the optimum duration of the pulse of fluid needs to be determined experimentally.

In FIG. 6c, no fluid is being ejected from the outlets 32, although suction is still being applied to draw the desorbed particles 92 into the inlet 38. Thus, in this embodiment, suction is continuously applied while the flow of fluid through the outlets 32 is switched on and off.

In summary, the preferred embodiments entail utilization of a combination of fluid ejection, such as blowing, and suction to collect chemical samples. To sample a chemical adsorbed on the surface 92, the apparatus relies on enhancing the number density of airborne molecules or particles 94 available for detection by the chemical sensor 52. As described above, the sample is taken by providing a controlled velocity pulse of fluid to disturb the surface 94 and desorb the particles 92, thereby suspending the particles in the region above the surface 94. During this time, the sample acquisition pump 58 can apply suction to draw the chemically enriched sample to the chemical sensor 52. This sample will be enriched with particles 94 desorbed from the surface 92. The apparatus is also useful for breaking up and sampling chemicals that have become crusted over with time.

The present invention may be embodied in other specific forms without departing from the essential characteristics as described herein. The embodiments described above are to be considered in all respects as illustrative only and not restrictive in any manner. The scope of the invention is, therefore, indicated by the following claims rather than the foregoing description. Any and all changes which come within the meaning and range of equivalency of the claims are to be considered in their scope.

What is claimed:

1. An apparatus for detecting particles that are adhered to a surface, comprising:
   an assembly having an outlet which ejects fluid for desorbing said particles from said surface, and having an inlet which collects a fluid sample comprising said desorbed particles;
   a chemical detector connected to receive said fluid sample; and
   a suction pump connected to draw the fluid sample across said chemical detector at a flow rate of 50–1000 cubic centimeters per minute.

2. The apparatus of claim 1, additionally comprising a blower for supplying fluid to said outlet.

3. The apparatus of claim 2, further comprising blower control electronics for activating said blower intermittently.

4. The apparatus of claim 1, additionally comprising a valve for providing an intermittent flow of said fluid through said outlet.

5. The apparatus of claim 1, additionally comprising a chamber wherein said fluid accumulates prior to being ejected from said outlet.

6. The apparatus of claim 1, additionally comprising a pump for drawing said particles into said inlet.

7. The apparatus of claim 6, further comprising pump control electronics for activating said pump intermittently.

8. The apparatus of claim 6, further comprising a valve for providing intermittent suction at said inlet.

9. The apparatus of claim 1, additionally comprising a second chamber connected to said inlet for receiving said desorbed particles.

10. The apparatus of claim 1, additionally comprising a heater for heating said fluid.

11. The apparatus of claim 1, additionally comprising a heater for heating said inlet.

12. The method of claim 1, wherein said outlet is oriented to direct said desorbed particles to said inlet.

13. The apparatus of claim 1, comprising a plurality of outlets arranged so as to direct said desorbed particles to said inlet.

14. The apparatus of claim 13, comprising a plurality of outlets arranged about a central inlet.

15. The apparatus of claim 1, wherein said outlet and said inlet share a common orifice.

16. The apparatus of claim 1, wherein said particles are electronically neutral.

17. The apparatus of claim 1, wherein said particles comprise molecules.

18. The apparatus of claim 1, wherein said fluid comprises a gas.

19. The apparatus of claim 18, wherein said fluid comprises ambient air.

20. The apparatus of claim 1, wherein said particles are in the form of an aerosol.

21. The apparatus of claim 1, wherein said assembly is comprised of surfaces coated with a chemically deactivating substance.

22. A method for collecting particles that are adhered to a surface and are to be detected using a chemical detector, comprising:
   ejecting fluid into said surface thereby desorbing said particles from said surface;
   drawing a fluid sample comprising said desorbed particles into an inlet; and
   passing said fluid sample through a passageway extending between the inlet and a chemical detector at a flow rate of 50–1000 cubic centimeters per minute.

23. The method of claim 22, wherein said ejecting comprises periodically blowing fluid onto said surface.

24. The method of claim 23, wherein said drawing comprises continuously providing suction throughout a plurality of blowing periods.

25. The method of claim 23, wherein said drawing comprises providing intermittent suction.

26. The method of claim 22, comprising heating said fluid.

27. The method of claim 22, comprising heating said desorbed particles.

28. The method of claim 27, wherein said heating said desorbed particles comprises heating said inlet.

29. The method of claim 22, wherein said ejecting comprises blowing said desorbed particles toward said inlet.

30. The method of claim 22, wherein said ejecting comprises blowing said fluid through said inlet to desorb said particles.

31. The method of claim 22, wherein said particles are electronically neutral.

32. The method of claim 22, wherein said particles comprise molecules.

33. The method of claim 22, wherein said fluid comprises a gas.

34. The method of claim 23, wherein said fluid comprises ambient air.

35. The method of claim 22, wherein said particles are in the form of a vapor.

36. The method of claim 22, wherein said drawing comprises passing said fluid over surfaces coated with a chemical deactivating substance.

37. A method for collecting particles that are adhered to a surface and are to be detected using a chemical detector, comprising:
   periodically blowing fluid onto said surface thereby desorbing said particles from said surface; and drawing said desorbed particles into an inlet, wherein said drawing and said blowing are alternated.

38. A portable apparatus for collecting particles that are adhered to a surface, comprising:

an assembly comprising a handle portion for positioning said apparatus, and a bottom portion having at least one outlet which ejects fluid for desorbing said particles from said surface, and at least one inlet which collects a fluid sample comprising said desorbed particles;

wherein said at least one outlet is oriented to direct substantially all of said fluid in a first direction and said at least one inlet is oriented to draw substantially all of the fluid sample in a second direction which is opposite to the first direction; and wherein said fluid in said first direction comprises a fluid pulse at a sufficiently low flow rate and time to enrich the air adjacent said inlet with desorbed particles when said bottom portion is positioned in spaced juxtaposition with said surface, and wherein the fluid sample is drawn at a flow rate of about 50 to 1000 cubic centimeters per minute to prevent substantial dilution of the fluid sample.

* * * * *